United States Patent

Ohlbach et al.

(10) Patent No.: US 6,905,997 B2
(45) Date of Patent: Jun. 14, 2005

(54) METHOD FOR GENERATING CATALYSTS

(75) Inventors: Frank Ohlbach, Düsseldorf (DE);
Hermann Luyken, Ludwigshafen (DE);
Andreas Ansmann, Wiesloch (DE);
Rolf-Hartmuth Fischer, Heidelberg (DE); Johann-Peter Melder,
Böhl-Iggelheim (DE); Peter Bassler,
Viernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 269 days.

(21) Appl. No.: 10/380,550

(22) PCT Filed: Sep. 20, 2001

(86) PCT No.: PCT/EP01/10849

§ 371 (c)(1),
(2), (4) Date: Mar. 17, 2003

(87) PCT Pub. No.: WO02/24334

PCT Pub. Date: Mar. 28, 2002

(65) Prior Publication Data

US 2003/0181313 A1 Sep. 25, 2003

(30) Foreign Application Priority Data

Sep. 25, 2000 (DE) .......................................... 100 47 703

(51) Int. Cl.⁷ ............................. B01J 38/50; B01J 38/10
(52) U.S. Cl. ........................................... 502/29; 502/53
(58) Field of Search ..................................... 502/29, 53

(56) References Cited

U.S. PATENT DOCUMENTS

| 4,322,315 | A |   | 3/1982  | Drake       |         |
|-----------|---|---|---------|-------------|---------|
| 5,230,791 | A | * | 7/1993  | Sherwood, Jr. | 208/213 |
| 5,648,305 | A | * | 7/1997  | Mansfield et al. | 502/27 |
| 5,674,797 | A | * | 10/1997 | Seppanen et al. | 502/33 |
| 5,789,621 | A |   | 8/1998  | Schnurr et al. |        |
| 6,080,883 | A |   | 6/2000  | Schnurr et al. |        |
| 6,278,023 | B1|   | 8/2001  | Voit et al.  |        |

FOREIGN PATENT DOCUMENTS

| EP | 521 716   | 1/1993  |
| WO | 97/37963  | 10/1997 |
| WO | 99/33561  | 7/1999  |

OTHER PUBLICATIONS

Houben–Weyl, Bd. 11/1 (Stickstoffverbindungen II, Amine), S. 545–574, 4. Auflage.

* cited by examiner

*Primary Examiner*—Stanley S. Silverman
*Assistant Examiner*—Jonas N. Strickland
(74) *Attorney, Agent, or Firm*—Novak Druce & Quigg, LLP

(57) ABSTRACT

A process is provided for the regeneration of a heterogeneous catalyst used for the preparation of compounds containing $NH_2$ groups by the hydrogenation, with hydrogen, of compounds containing at least one unsaturated carbon-nitrogen bond, wherein a) the feed of the compound to be hydrogenated is stopped and
b) the heterogeneous catalyst is treated with a compound of the formula $$R^1R^2N\text{---}CO\text{---}R^3 \qquad (I),$$

in which $R^1$ is hydrogen or $C_1$–$C_4$ alkyl and $R^2$, $R^3$ independently of one another are each hydrogen or $C_1$–$C_4$ alkyl or together are a $C_3$–$C_6$ alkylene group, or mixtures of such compounds, at a pressure ranging from 0.1 to 30 MPa and a temperature ranging from 100 to 300° C., with the proviso that the compound of formula (I) is in liquid form during the treatment.

11 Claims, No Drawings

METHOD FOR GENERATING CATALYSTS

The present invention relates to a process for the regeneration of a heterogeneous catalyst used for the preparation of compounds containing NH$_2$ groups by the hydrogenation, with hydrogen, of compounds containing at least one unsaturated carbon-nitrogen bond, wherein a) the feed of the compound to be hydrogenated is stopped and b) the heterogeneous catalyst is treated with a compound of formula

$$R^1R^2N\text{—}CO\text{—}R^3 \qquad (I),$$

in which

R$^1$ is hydrogen or C$_1$–C$_4$ alkyl and

R$^2$, R$^3$ independently of one another are each hydrogen or C$_1$–C$_4$ alkyl or together are a C$_3$–C$_6$ alkylene group, or mixtures of such compounds, at a pressure ranging from 0.1 to 30 MPa and a temperature ranging from 100 to 300° C., with the proviso that the compound of formula (I) is in liquid form during the treatment.

Processes for the preparation of compounds containing NH$_2$ groups by the hydrogenation, with hydrogen, of compounds containing at least one unsaturated carbon-nitrogen bond, in the presence of a heterogeneous catalyst, are generally known, for example from Houben-Weyl, Vol. 11/1 (Nitrogen Compounds II, Amines), pp. 545–574, 4$^{th}$ edition, 1957.

WO 97/37963, WO 97/37964, WO 98/04515 and DE-A-198 09 688 disclose processes for the hydrogenation of adipodinitrile to hexamethylenediamine, or mixtures containing 6-aminocapronitrile and hexamethylenediamine, in the presence of heterogeneous catalysts based on iron, cobalt or nickel or compounds thereof. In such processes, relevant catalyst properties, such as activity or selectivity, deteriorate with operating time.

Although a drop in activity can be compensated by raising the reaction temperature, the disadvantage here is that the selectivity of a catalyst conventionally decreases with increasing reaction temperature and, in addition, the higher temperature accelerates the further drop in activity.

Processes are known for the regeneration of a catalyst whose relevant properties, such as activity or selectivity, have deteriorated with operating time. Regeneration is understood here as meaning a process by which said catalyst properties can be improved again. Thus WO 97/37963, WO 97/37964 and WO 98/04515 describe processes for the regeneration of a heterogeneous catalyst (whose activity and selectivity have dropped) used for the preparation of compounds containing NH$_2$ groups by the hydrogenation, with hydrogen, of compounds containing at least one unsaturated carbon-nitrogen bond, by treatment with hydrogen under defined process conditions.

Although these regeneration processes give a good result in terms of improving the selectivity and activity, it would be desirable to protect the catalyst by reducing the temperature and time required for the regeneration.

It is an object of the present invention to provide a process for the regeneration of a heterogeneous catalyst used for the preparation of compounds containing NH$_2$ groups by the hydrogenation, with hydrogen, of compounds containing at least one unsaturated carbon-nitrogen bond, said process affording the regeneration in a technically simple and economic manner while avoiding said disadvantages.

We have found that this object is achieved by the process defined at the outset.

The heterogeneous catalysts to be regenerated have previously been used for the preparation of compounds containing NH$_2$ groups by the hydrogenation, with hydrogen, of compounds containing at least one unsaturated carbon-nitrogen bond.

As compounds [lacuna] at least one unsaturated carbon-nitrogen bond such as a carbon-nitrogen double or triple bond, it is preferred to use a C$_4$–C$_8$ alkyl nitrile or dinitrile or mixtures of such nitrites or dinitriles, such as butane nitrile, pentane nitrile, hexane nitrile, heptane nitrile, octane nitrile, butane dinitrile, pentane dinitrile, hexane dinitrile, heptane dinitrile and octane dinitrile, particularly preferably terminal C$_4$–C$_8$ dinitriles such as 1,4-dicyanobutane ("adipodinitrile"), 1,5-dicyanopentane, 1,6-dicyanohexane, 1,7-dicyanoheptane and 1,8-dicyanooctane, C$_5$–C$_8$ cycloalkyl nitrites or dinitriles such as cyclopentyl nitrile, cyclohexyl nitrile, cycloheptyl nitrile, cyclooctyl nitrile, cyclopentyl dinitrile, cyclohexyl dinitrile, cycloheptyl dinitrile and cyclooctyl dinitrile, or amino nitrites containing from 4 to 8 carbon atoms, preferably alpha,omega-amino nitrites such as 5-aminovaleronitrile and 6-aminocapronitrile.

The nitrites, dinitriles and amino nitrites can also carry other functional groups provided that they do not detract from the hydrogenation or that simultaneous or partial hydrogenation is desired. Examples which may be mentioned are C$_1$–C$_4$ alkyl groups, aryl groups, especially phenyl, C$_5$–C$_8$ cycloalkyl, aminoalkyl, N-alkylaminoalkyl, N-(cyanomethyl)aminoalkyl and the imino group (C=NH, C=NR), preferably the imino group.

Adipodinitrile, 6-aminocapronitrile, 3-cyano-3,5,5-trimethylcyclohexylimine, NC—(CH$_2$)$_2$—NH—(CH$_2$)$_2$—CN, NC—(CH$_2$)$_2$—NH—(CH$_2$)$_2$—NH—(CH$_2$)$_2$—CN and 1-cyano-2-aminoethane are especially suitable, adipodinitrile being particularly preferred.

In one advantageous embodiment, adipodinitrile can be hydrogenated to hexamethylenediamine.

In another advantageous embodiment, adipodinitrile can be hydrogenated to a mixture containing hexamethylenediamine and 6-aminocapronitrile.

On the basis of previous observations in respect of the catalytically active component, suitable heterogeneous catalysts to be regenerated are any heterogeneous catalysts known for the preparation of compounds containing NH$_2$ groups by the hydrogenation, with hydrogen, of compounds containing at least one unsaturated carbon-nitrogen bond.

In one preferred embodiment, it is possible to use a heterogeneous catalyst containing, as the catalytically active component, an element selected from the group consisting of iron, cobalt and nickel or mixtures thereof, particularly preferably iron or cobalt or mixtures thereof, and very particularly preferably iron.

In another preferred embodiment, it is possible to use a heterogeneous catalyst containing, as the catalytically active component, a compound of an element selected from the group consisting of iron, cobalt and nickel or mixtures thereof, particularly preferably iron or cobalt or mixtures thereof, and very particularly preferably iron.

Such catalysts can be used unsupported, especially for fixed bed or suspension methods, for example in the form of Raney catalysts or other unsupported forms (so-called unsupported catalysts). The unsupported forms can contain small amounts of auxiliary substances compared with the high content of active component. These auxiliary substances can have favorable effects either on the catalytic activity and/or selectivity or on the catalyst properties such as hardness, abrasion or chemical or thermal stability. The total amount of auxiliary substances generally ranges from 0 to 20% by weight, based on the amount of active component. Auxiliary substances which can be used are oxides, phosphates and sulfates of alkali metal and alkaline earth metal compounds, thermally stable oxides such as silicon dioxide, aluminum oxide, titanium dioxide and zirconium dioxide, and other transition metal oxides. It is also possible to use supported catalysts. Suitable supports are generally ceramic supports such as aluminum oxide, silicon dioxide, titanium dioxide and zirconium dioxide, or silicon carbide or activated carbon. In supported catalysts, the content of active component normally ranges from 3 to 95% by weight, preferably from 30 to 95% by weight, based on the support.

If desired, the catalysts can also be modified with metals of group VIB (Cr, Mo, W) and group VIII (Ru, Os, Rh, Ir, Pd, Pt) of the Periodic Table of the Elements, and with copper, manganese and rhenium, the content of the non-modifying part of the active component generally ranging from 50 to 99.9% by weight, preferably from 80 to 99% by weight, based on the whole active component.

Furthermore, the catalysts can be modified with a compound based on an alkali metal or alkaline earth metal such as lithium, sodium, potassium, rubidium, cesium, magnesium, calcium, strontium or barium. The chosen weight ratio conventionally ranges from 0 to 5% by weight, preferably from 0.1 to 3% by weight, of alkali metal or alkaline earth metal, based on the non-modifying part of the active component.

Furthermore, in the case of catalysts whose active component are [sic] based on iron or an iron compound, the catalysts can be modified with a compound based on 1, 2, 3, 4 or 5 elements selected from the group consisting of aluminum, silicon, zirconium, titanium and vanadium. The chosen weight ratio is conventionally 0 to 3% by weight of modifying agent, based on the iron.

Furthermore, in the case of catalysts whose active component are [sic] based on iron or an iron compound, the catalysts can be modified with a compound based on manganese. The chosen manganese concentration is conventionally 0 to 25% by weight, preferably 0.01 to 5% by weight, based on the iron.

Such catalysts and their preparation are known per se, for example from WO 97/37963, WO 97/37964, WO 98/04515 and DE-A-198 09 688.

Before being used, the catalysts can be activated, for example by treatment with hydrogen, the activation being carried out in a manner known per se under atmospheric pressure or superatmospheric pressure and at temperatures above 200° C.

The hydrogenation can be carried out by the liquid phase, trickle or suspension method.

If the hydrogenation is carried out in suspension, the chosen temperatures conventionally range from 40 to 150° C., preferably from 50 to 100° C. and particularly preferably from 60 to 90° C.; the chosen pressure generally ranges from 2 to 20 MPa, preferably from 3 to 10 MPa and particularly preferably from 4 to 9 MPa. The residence times depend essentially on the desired yield and selectivity and the desired conversion; the residence time is conventionally chosen so as to achieve the maximum yield, ranging for example from 50 to 275 min, preferably from 70 to 200 min.

In the suspension method, a liquid diluent can also be added, suitable liquid diluents preferably being ammonia, amines, diamines and triamines having from 1 to 12 carbon atoms, such as trimethylamine, triethylamine, tripropylamine or tributylamine, or alcohols, especially methanol or ethanol; ammonia is particularly preferred. The chosen concentration of compound to be hydrogenated ranges appropriately from 10 to 90% by weight, preferably from 30 to 80% by weight and particularly preferably from 40 to 70% by weight, based on the sum of compound to be hydrogenated and liquid diluent.

The chosen amount of catalyst generally ranges from 1 to 50% by weight, preferably from 5 to 20% by weight, based on the amount of compound to be hydrogenated.

The suspension hydrogenation can be carried out batchwise or continuously, preferably continuously, and normally in the liquid phase.

The hydrogenation can also be carried out batchwise or continuously, preferably continuously, in a fixed bed reactor by the trickle or liquid phase method, the chosen temperature conventionally ranging from 30 to 200° C., preferably from 50 to 150° C., and the chosen pressure normally ranging from 2 to 30 MPa, preferably from 3 to 20 MPa. The hydrogenation is preferably carried out in the presence of a liquid diluent, preferably ammonia, amines, diamines and triamines having from 1 to 12 carbon atoms, such as trimethylamine, triethylamine, tripropylamine or tributylamine, or alcohols, especially methanol or ethanol, and particularly preferably ammonia.

In one preferred embodiment, the chosen ammonia content ranges from 0.5 to 10 g, preferably from 1 to 6 g, per gram of compound to be hydrogenated, especially adipodinitrile.

Preferably, the chosen catalyst loading ranges from 0.1 to 2.0 kg, preferably from 0.3 to 1.0 kg, of compound to be hydrogenated/l×h, especially adipodinitrile/l×h. Here again, the conversion and hence the selectivity can be specifically adjusted by changing the residence time.

The hydrogenation can be carried out in a conventional reactor suitable for this purpose.

If the reaction is carried out in the gas phase, the chosen temperatures conventionally range from 100 to 250° C., preferably from 160 to 200° C.; the chosen pressure generally ranges from 0.01 to 3 MPa, preferably from 0.09 to 0.5 MPa. Also, the amount of hydrogen used is normally 2 to 300 mol, preferably 10 to 200 mol, per mol of compound containing at least one unsaturated carbon-nitrogen bond.

In one preferred embodiment, the hydrogenation of the compound to be hydrogenated, especially adipodinitrile, is carried out in the presence of ammonia as the liquid diluent with fixed bed catalysts.

The catalyst is regenerated by first stopping the feed of compound to be hydrogenated, especially adipodinitrile, and the feed of liquid diluent, if used. The catalyst and the reaction mixture can advantageously be separated.

The hydrogen feed can also be stopped, the catalyst advantageously being regenerated in the presence of hydrogen.

According to the invention, the catalyst to be regenerated is treated with a compound of formula (I):

$$R^1R^2N-CO-R^3 \qquad (I),$$

or mixtures of such compounds.

In this formula, $R^1$ is hydrogen or a $C_1$–$C_4$ alkyl such as methyl, ethyl, n-propyl, i-propyl, n-butyl, i-butyl, s-butyl or t-butyl, preferably hydrogen or methyl.

$R^2$, $R^3$ independently of one another are each hydrogen or $C_1$–$C_4$ alkyl such as methyl, ethyl, n-propyl, i-propyl, n-butyl, i-butyl, s-butyl or t-butyl, preferably hydrogen or methyl, or together are a $C_3$–$C_6$ alkylene group of the type —$(CH_2)_n$—, in which n can take a value of 3, 4, 5 or 6, preferably 3.

In the case where they are not hydrogen, the groups $R^1$, $R^2$ and $R^3$ can be substituents such as aryl groups, especially phenyl, $C_5$–$C_8$ cycloalkyl, aminoalkyl and, if the group $R^1$, $R^2$ or $R^3$ in question is not methyl, $C_1$–$C_4$ alkyl groups.

In the case where they are not hydrogen, the groups $R^1$, $R^2$ and $R^3$ can carry functional groups such as halogens, for example fluorine, chlorine or bromine.

The groups $R^1$, $R^2$ and $R^3$ preferably carry no functional groups.

In one preferred embodiment, $R^2$ and $R^3$ together are a $C_3$ alkylene group of the type —$(CH_2)_3$—.

In another preferred embodiment, $R^2$ and $R^3$ together are a $C_3$ alkylene group of the type —$(CH_2)_3$— and $R^1$ is a methyl group.

In another preferred embodiment, $R^1$ and $R^2$ are each a methyl group and $R^3$ is hydrogen.

According to the invention, the heterogeneous catalyst is treated with a compound of formula (I) with the proviso that said compound is in liquid form during the treatment.

Treatment is understood as meaning the batchwise or continuous contacting of the catalyst with a compound of formula (I).

If the catalyst is a suspension catalyst, it can advantageously be suspended in a compound of formula (I), which can be introduced into the catalyst continuously or batchwise. The compound of formula (I) can be separated from the catalyst continuously or batchwise.

If the catalyst is a fixed bed catalyst, it can be removed from the reactor prior to regeneration. In one advantageous embodiment, the regeneration can be effected in the hydrogenation reactor without removing the catalyst.

If the catalyst is a fixed bed catalyst, a compound of formula (I) can advantageously be passed through it continuously or batchwise. The compound of formula (I) can be introduced into the catalyst continuously or batchwise and can be separated from the catalyst continuously or batchwise.

The compound of formula (I) separated from the catalyst can be discarded or, advantageously, recycled into the catalyst, optionally after purification.

According to the invention, the regeneration is effected at a pressure ranging from 0.1 to 30 MPa. If this is done in the presence of hydrogen, the regeneration can advantageously be effected at the pressure previously applied during the hydrogenation. If the regeneration is continuous, the appropriate amount of hydrogen advantageously ranges from 1 to 100 g, preferably from 2 to 50 g, of hydrogen/l of reactor volume×hour.

The regeneration can be effected at temperatures of at least 100° C., preferably of at least 120° C., particularly preferably of at least 140° C. and very particularly preferably of at least 160° C.

The appropriate upper temperature limit for the regeneration is the decomposition point of the compound of formula (I), i.e. generally 300° C., and is preferably at most 200° C. and particularly preferably at most 180° C.

The duration of treatment of the catalyst to be regenerated is generally 1 to 12 hours, preferably 2 to 4 hours.

After the treatment, the regenerated catalyst and the compound of formula (I) are separated from one another. The regenerated catalyst can then be re-used, like a freshly prepared catalyst, in a process for the preparation of compounds containing $NH_2$ groups by the hydrogenation, with hydrogen, of compounds containing at least one unsaturated carbon-nitrogen bond.

EXAMPLES

Example 1

Three tubular reactors connected in series (total length= 4.5 m, d=6 mm) were filled with 142 ml (240 g) of an iron-based catalyst prepared according to Example 1a of DE-A-198 09 688 (1.5 to 3 mm chips), which was then reduced in a stream of hydrogen (200 l/h) under atmospheric pressure, the temperature being raised from 70° C. to 340° C. over 24 hours and then kept at 340° C. for 72 hours.

After the temperature had dropped, a mixture of 0.66 mol/h of adipodinitrile, 365 ml/h of ammonia and 1.05 mol/h of hydrogen was introduced into the reactor. The reactor temperature was adjusted so that the total selectivity in respect of 6-aminocapronitrile and hexamethylenediamine was constant at a pressure of 25 MPa. This was done by setting the temperature at 94° C. initially and raising it to 107° C. over 9000 hours.

The feeds were then stopped and the catalyst was flushed for four hours at 160° C. with 100 ml/h of N-methyl-alpha-pyrrolidone.

It was then flushed for four hours at 107° C. with 365 ml/h of ammonia, after which the original feeds were restarted. The reactor temperature could be lowered to 94° C. in order to achieve the total selectivity obtained prior to regeneration.

Example 2

In a continuously operated tubular reactor, adipodinitrile was hydrogenated to a mixture of 6-aminocapronitrile and hexamethylenediamine at 70 bar and at a loading of 0.22 kg/l×h of Cr-doped Raney Co chips having a size of 1–3 mm, in the presence of ammonia as solvent.

After an operating time of 80 h, the adipodinitrile conversion was 92.8% at a mean temperature of 37.0° C. over the length of the reactor.

After an operating time of 2004 h, the catalyst had continuously lost activity to give an adipodinitrile conversion of only 59.9% at a mean temperature of 48.5° C. over the length of the reactor.

The catalyst was regenerated by stopping the feeds of adipodinitrile and ammonia and flushing the catalyst for 4 hours with N-methyl-alpha-pyrrolidone at a loading of 2 kg/l×h and at 150° C., the hydrogen feed being maintained at 500 Nl/l×h and the pressure being maintained at 70 bar. After the regeneration, the reactor was cooled and started up again as with a fresh catalyst.

After a total operating time of 2112 h, the adipodinitrile conversion was 91.4% and the initial total selectivity in respect of 6-aminocapronitrile and hexamethylenediamine was achieved at a mean temperature of 37.3° C. over the length of the reactor.

We claim:

1. A process for the regeneration of a heterogeneous catalyst used for the preparation of compounds containing $NH_2$ groups by the hydrogenation, with hydrogen, of compounds containing at least one unsaturated carbon-nitrogen bond, wherein a) the feed of the compound to be hydrogenated is stopped and b) the heterogeneous catalyst is treated with a compound of formula (I):

$$R^1R^2N\text{—}CO\text{—}R^3 \tag{I}$$

in which $R^1$ is hydrogen or $C_1$–$C_4$ alkyl and $R^2$, $R^3$ independently of one another are each hydrogen or $C_1$–$C_4$ alkyl or together are a $C^3$–$C^6$ alkylene group, or mixtures of such compounds, at a pressure ranging from 0.1 to 30 MPa and a temperature ranging from 100 to 300°, with the proviso that the compound of formula (I) is in liquid form during the treatment.

2. A process as claimed in claim 1 wherein the heterogeneous catalyst regenerated has been used for the hydrogenation of adipodinitrile.

3. A process as claimed in claim 1 wherein the heterogeneous catalyst regenerated has been used for the hydrogenation of adipodinitrile to hexamethylenediamine.

4. A process as claimed in claim 1 wherein the heterogeneous catalyst regenerated has been used for the hydrogenation of adipodinitrile to a mixture containing hexamethylenediamine and 6-aminocapronitrile.

5. A process as claimed in claim 1 wherein, in formula (I), $R^2$ and $R^3$ together form a $C_3$ alkylene group.

6. A process as claimed in claim 1 wherein, in formula (I), $R^2$ and $R^3$ together are a $C_3$ alkylene group and $R^1$ is a methyl group.

7. A process as claimed in claim 1 wherein, in formula (I), $R^1$ and $R^2$ are each a methyl group and $R^3$ is hydrogen.

8. A process as claimed in claim 1 wherein the heterogeneous catalyst contains, as the catalytically active component, an element selected from the group consisting of iron, cobalt and nickel or mixtures thereof.

9. A process as claimed in claim 1 wherein the heterogeneous catalyst contains, as the catalytically active component, a compound of an element selected from the group consisting of iron, cobalt and nickel or mixtures thereof.

10. A process as claimed in claim 1 wherein the regeneration is effected in the presence of hydrogen.

11. A process as claimed in claim 1 wherein the hydrogen feed is stopped in step a).

* * * * *

UNITED STATES PATENT AND TRADEMARK OFFICE
CERTIFICATE OF CORRECTION

| | |
|---|---|
| PATENT NO. | : 6,905,997 B2 |
| APPLICATION NO. | : 10/380550 |
| DATED | : June 14, 2005 |
| INVENTOR(S) | : Frank Ohbach et al. |

It is certified that error appears in the above-identified patent and that said Letters Patent is hereby corrected as shown below:

<u>Column 6,</u>
Line 65, "$C^3 - C^6$ alkylene" should read -- $C_3 - C_6$ alkylene --.

Signed and Sealed this

Twenty-seventh Day of June, 2006

JON W. DUDAS
*Director of the United States Patent and Trademark Office*